US006697658B2

(12) United States Patent
Al-Ali

(10) Patent No.: US 6,697,658 B2
(45) Date of Patent: Feb. 24, 2004

(54) LOW POWER PULSE OXIMETER

(75) Inventor: Ammar Al-Ali, Tustin, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 10/184,028

(22) Filed: Jun. 26, 2002

(65) Prior Publication Data

US 2003/0028085 A1 Feb. 6, 2003

Related U.S. Application Data

(60) Provisional application No. 60/302,564, filed on Jul. 2, 2001.

(51) Int. Cl.[7] ................................. A61B 5/00
(52) U.S. Cl. ....................... 600/323; 600/336
(58) Field of Search ................... 600/310, 322, 600/323, 333, 336

(56) References Cited

U.S. PATENT DOCUMENTS 5,924,979 A    7/1999  Swedlow et al.
6,088,607 A    7/2000  Diab et al.

FOREIGN PATENT DOCUMENTS

EP     0 872 210 A1    10/1998
WO     WO 99/63883     12/1999

*Primary Examiner*—Eric F. Winakur
(74) *Attorney, Agent, or Firm*—Knobbe Martens Olson & Bear LLP

(57) ABSTRACT

A pulse oximeter adaptively samples an input signal from a sensor in order to reduce power consumption in the absence of overriding conditions. Various sampling mechanisms may be used individually or in combination, including reducing the duty cycle of a drive current to a sensor emitter, intermittently powering-down a front-end interface to a sensor detector, or increasing the time shift between processed data blocks. Both internal parameters and output parameters may be monitored to trigger or override a reduced power consumption state. In this manner, a pulse oximeter can lower power consumption without sacrificing performance during, for example, high noise conditions or oxygen desaturations.

19 Claims, 11 Drawing Sheets

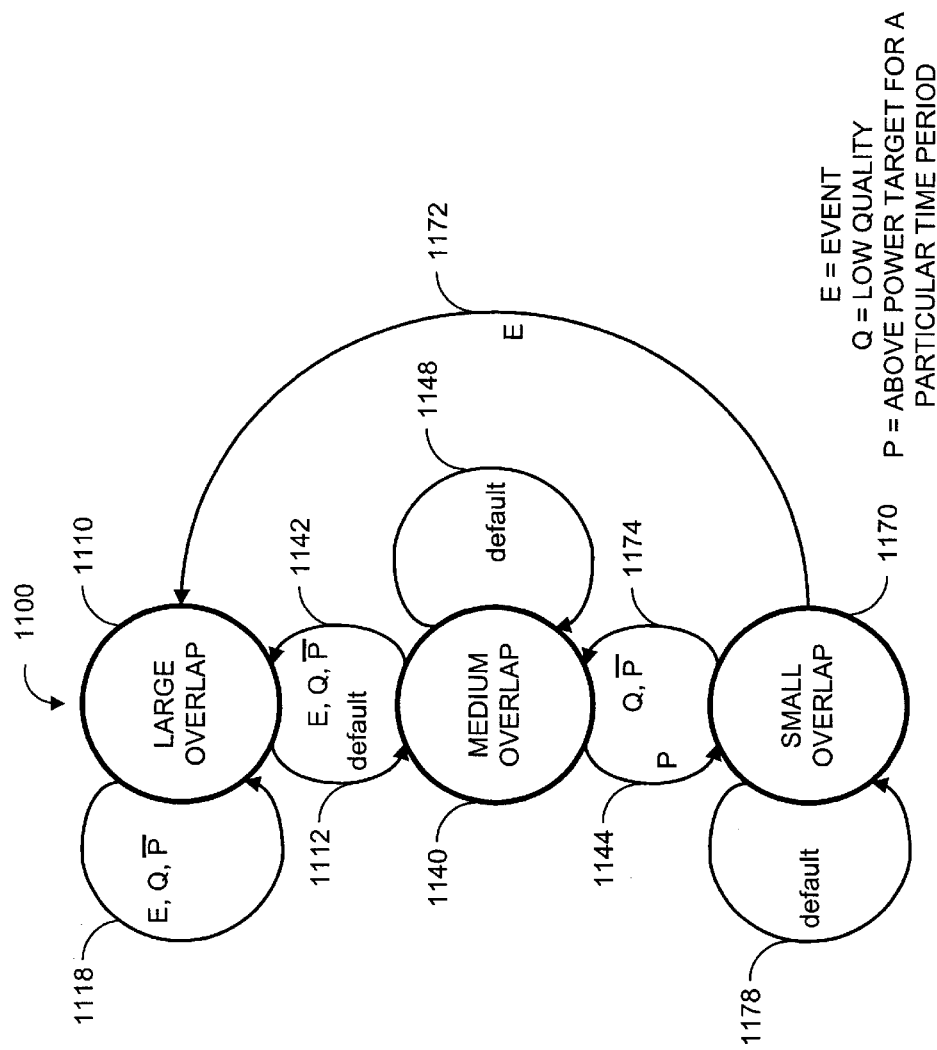

LOW POWER PULSE OXIMETER

REFERENCE TO RELATED APPLICATIONS

This application relates to and claims the benefit of prior provisional application No. 60/302,564 entitled "Low Power Pulse Oximeter," filed Jul. 2, 2001 and incorporated by reference herein.

BACKGROUND OF THE INVENTION

Pulse oximetry is a widely accepted noninvasive procedure for measuring the oxygen saturation level of a person's arterial blood, an indicator of their oxygen supply. Oxygen saturation monitoring is crucial in critical care and surgical applications, where an insufficient blood supply can quickly lead to injury or death. FIG. 1 illustrates a conventional pulse oximetry system 100, which has a sensor 110 and a monitor 150. The sensor 110, which can be attached to an adult's finger or an infant's foot, has both red and infrared LEDs 112 and a photodiode detector 114. For a finger, the sensor is configured so that the LEDs 112 project light through the fingernail and into the blood vessels and capillaries underneath. The photodiode 114 is positioned at the finger tip opposite the fingernail so as to detect the LED emitted light as it emerges from the finger tissues. A pulse oximetry sensor is described in U.S. Pat. No. 6,088,607 entitled "Low Noise Optical Probe," which is assigned to the assignee of the present invention and incorporated by reference herein.

Also shown in FIG. 1, the monitor 150 has LED drivers 152, a signal conditioning and digitization front-end 154, a signal processor 156, a display driver 158 and a display 159. The LED drivers 152 alternately activate the red and IR LEDs 112 and the front-end 154 conditions and digitizes the resulting current generated by the photodiode 114, which is proportional to the intensity of the detected light. The signal processor 156 inputs the conditioned photodiode signal and determines oxygen saturation based on the differential absorption by arterial blood of the two wavelengths emitted by the LEDs 112. Specifically, a ratio of detected red and infrared intensities is calculated by the signal processor 156, and an arterial oxygen saturation value is empirically determined based on the ratio obtained. The display driver 158 and associated display 159 indicate a patient's oxygen saturation, heart rate and plethysmographic waveform.

SUMMARY OF THE INVENTION

Increasingly, pulse oximeters are being utilized in portable, battery-operated applications. For example, a pulse oximeter may be attached to a patient during emergency transport and remain with the patient as they are moved between hospital wards. Further, pulse oximeters are often implemented as plug-in modules for multiparameter patient monitors having a restricted power budget. These applications and others create an increasing demand for lower power and higher performance pulse oximeters. A conventional approach for reducing power consumption in portable electronics, typically utilized by devices such as calculators and notebook computers, is to have a "sleep mode" where the circuitry is powered-down when the devices are idle.

FIG. 2 illustrates a sleep-mode pulse oximeter 200 utilizing conventional sleep-mode power reduction. The pulse oximeter 200 has a pulse oximeter processor 210 and a power control 220. The power control 220 monitors the pulse oximeter output parameters 212, such as oxygen saturation and pulse rate, and controls the processor power 214 according to measured activity. For example, if there is no significant change in the oxygen saturation value over a certain time period, the power control 220 will power down the processor 210, except perhaps for a portion of memory. The power control 220 may have a timer that triggers the processor 210 to periodically sample the oxygen saturation value, and the power control 220 determines if any changes in this parameter are occurring. If not, the power control 220 will leave the processor 210 in sleep mode.

There are a number of disadvantages to applying consumer electronic sleep mode techniques to pulse oximetry. By definition, the pulse oximeter is not functioning during sleep mode. Unlike consumer electronics, pulse oximetry cannot afford to miss events, such as patient oxygen desaturation. Further, there is a trade-off between shorter but more frequent sleep periods to avoid a missed event and the increased processing overhead to power-up after each sleep period. Also, sleep mode techniques rely only on the output parameters to determine whether the pulse oximeter should be active or in sleep mode. Finally, the caregiver is given no indication of when the pulse oximeter outputs were last updated.

One aspect of a low power pulse oximeter is a sensor interface adapted to drive a pulse oximetry sensor and receive a corresponding input signal. A processor derives a physiological measurement corresponding to the input signal, and a display driver communicates the measurement to a display. A controller generates a sampling control output to at least one of said sensor interface and said processor so as to reduce the average power consumption of the pulse oximeter consistent with a predetermined power target.

In one embodiment, a calculator derives a signal status output responsive to the input signal. The signal status output is communicated to the controller to override the sampling control output. The signal status output may indicate the occurrence of a low signal quality or the occurrence of a physiological event. In another embodiment, the sensor interface has an emitter driver adapted to provide a current output to an emitter portion of the sensor. Here, the sampling control output determines a duty cycle of the current output. In a particular embodiment, the duty cycle may be in the range of about 3.125% to about 25%.

In another embodiment, the sensor interface has a front-end adapted to receive the input signal from a detector portion of the sensor and to provide a corresponding digitized signal. Here, the sampling control output determines a powered-down period of the front-end. A confidence indicator responsive to a duration of the powered-down period may be provided and displayed.

In yet another embodiment, the pulse oximeter comprises a plurality of data blocks responsive to the input signal, wherein the sampling control output determines a time shift of successive ones of the data blocks. The time shift may vary in the range of about 1.2 seconds to about 4.8 seconds.

An aspect of a low power pulse oximetry method comprises the steps of setting a power target and receiving an input signal from a pulse oximetry sensor. Further steps include calculating signal status related to the input signal, calculating power status related to the power target, and sampling based upon the result of the calculating signal status and the calculating power status steps.

In one embodiment, the calculating signal status step comprises the substeps of receiving a signal statistic related to the input signal, receiving a physiological measurement related to the input signal, determining a low signal quality condition from the signal statistic, determining an event occurrence from the physiological measurement, and indicating an override based upon the low signal quality condition or the event occurrence. The calculating power status step may comprise the substeps of estimating an average power consumption for at least a portion of the pulse oximeter, and indicating an above power target condition when the average power consumption is above the power target. The sampling step may comprise the substep of increasing sampling as the result of the override. The sampling step may also comprise the substep of decreasing sampling as the result of the above power target condition, except during the override.

Another aspect of a low power pulse oximetry method comprises the steps of detecting an override related to a measure of signal quality or a physiological measurement event, increasing the pulse oximeter power to a higher power level when the override exists, and reducing the pulse oximeter power to a lower power level when the override does not exist. The method may comprise the further steps of predetermining a target power level for a pulse oximeter and cycling between the lower power level and the higher power level so that an average pulse oximeter power is consistent with the target power level.

In one embodiment, the reducing step comprises the substep of decreasing the duty cycle of an emitter driver output to the sensor. In another embodiment, the reducing step comprises the substep of powering-down a detector front-end. A further step may comprise displaying a confidence indicator related to the duration of the powering-down substep. In yet another embodiment, the reducing step comprises the substep of increasing the time-shift of post-processor data blocks.

Another aspect of a low power pulse oximeter comprises a sensor interface adapted to receive an input signal from a sensor, a signal processor configured to communicate with the sensor interface and to generate an internal parameter responsive to the input signal, and a sampling controller responsive to the internal parameter so as to generate a sampling control to alter the power consumption of at least one of the sensor interface and the signal processor. The signal processor may be configured to generate an output parameter and the sampling controller may be responsive to a combination of the internal and output parameters so as to generate a sampling control to alter the power consumption of at least one of the sensor interface and the signal processor. The internal parameter may be indicative of the quality of the input signal. The output parameter may be indicative of oxygen saturation.

In another embodiment, the sampling controller is responsive to a predetermined power target in combination with the internal parameter so as to generate a sampling control to alter the power consumption of at least one of the sensor interface and the signal processor. The signal processor may be configured to generate an output parameter and the sampling controller may be responsive to a combination of the internal and output parameters and the power target so as to generate a sampling control to alter the power consumption of at least one of the sensor interface and the signal processor. The sensor interface may comprise an emitter driver and the sampling control may modify a duty cycle of the emitter driver. The sensor interface may comprise a detector front-end and the sampling control may intermittently power-down the detector front-end. The processor may generate a plurality of data blocks corresponding to the input signal, where each of the data blocks have a time shift from a preceding one of the data blocks, and where the sampling control may determine the amount of the time shift.

A further aspect of a low power pulse oximeter comprises an interface means for communicating with a sensor, a processor means for generating an internal parameter and an output parameter, and a controller means for selectively reducing the power consumption of at least one of the interface means and the processor means based upon the parameters. In one embodiment, the interface means comprises a driver means for determining the duty cycle of emitter current to the sensor, the driver means being responsive to the controller means. In another embodiment, the interface means comprises a detector front-end means for receiving an input signal from the sensor, the power for the detector front-end means being responsive to the controller means. In yet another embodiment, the processor means comprises a post-processor means for determining a time shift between data blocks, the post-processor means being responsive to the controller means. In a further embodiment, the controller means comprises a signal status calculator means for generating an indication of a low signal quality or a physiological event based upon at least one of an internal signal statistic and an output physiological measurement, and a control engine means in communications with the signal status calculator means for generating a sampling control responsive to the indication. In yet a further embodiment, the controller means comprises a power status calculator means for generating a power indication of power consumption relative to a power target, and a control engine means in communications with the power status calculator means for generating a sampling control responsive to the power indication.

BRIEF DESCRIPTION OF THE DRAWINGS

FIG. 11 is a state diagram of the sampling controller for variable data block overlap processing.

DETAILED DESCRIPTION OF THE PREFERRED EMBODIMENT

Figure 1:
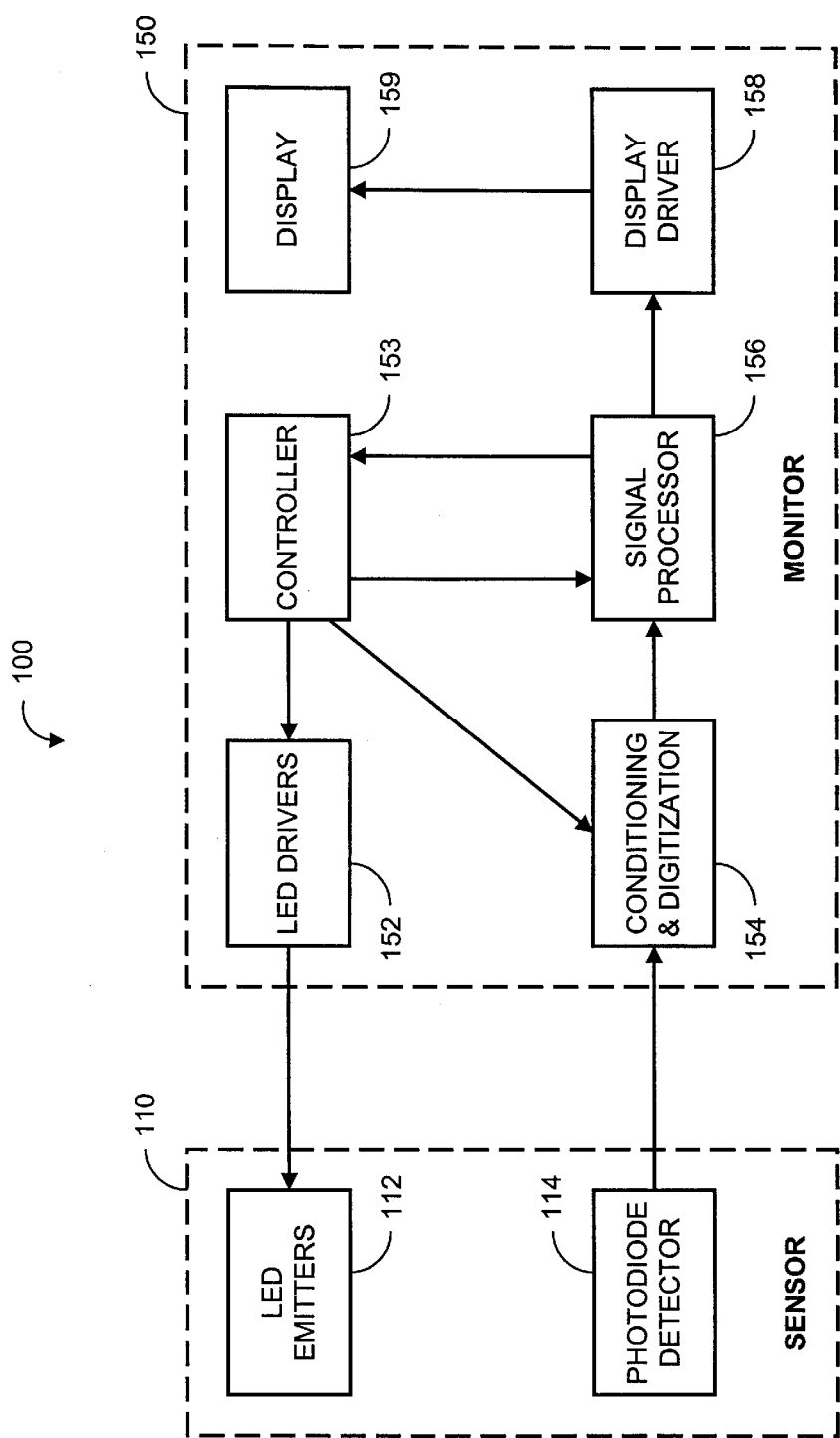
FIG. 1 is a block diagram of a conventional pulse oximeter sensor and monitor.
Figure 2:
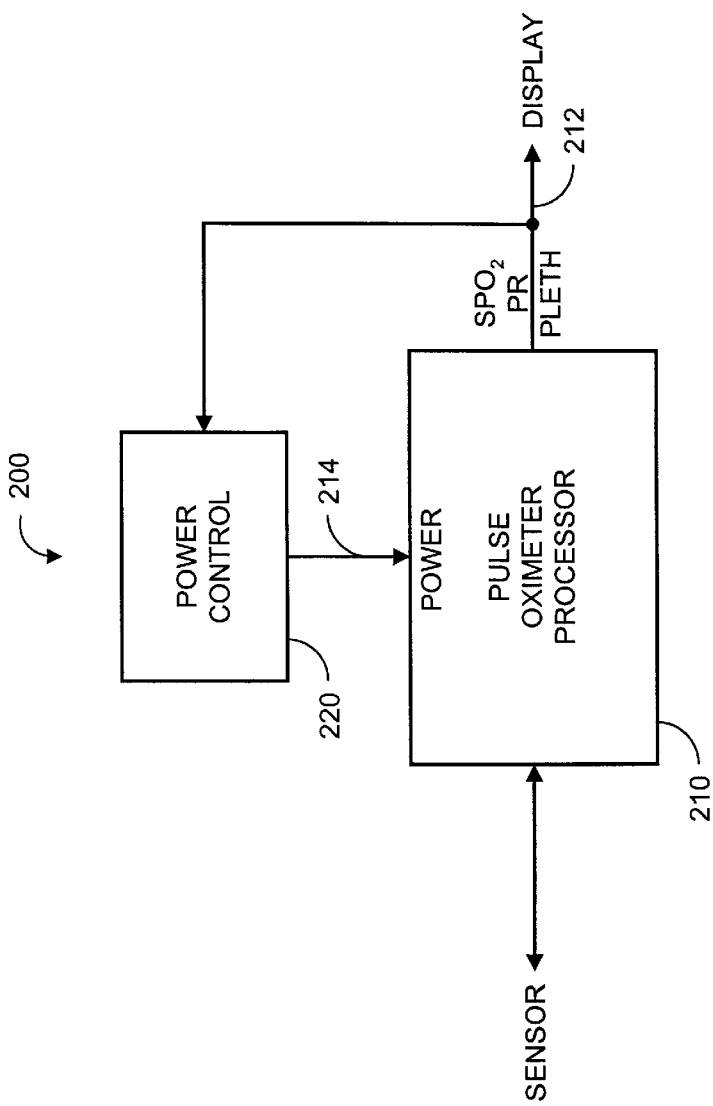
FIG. 2 is a block diagram of a pulse oximeter having a conventional sleep mode.
Figure 3:
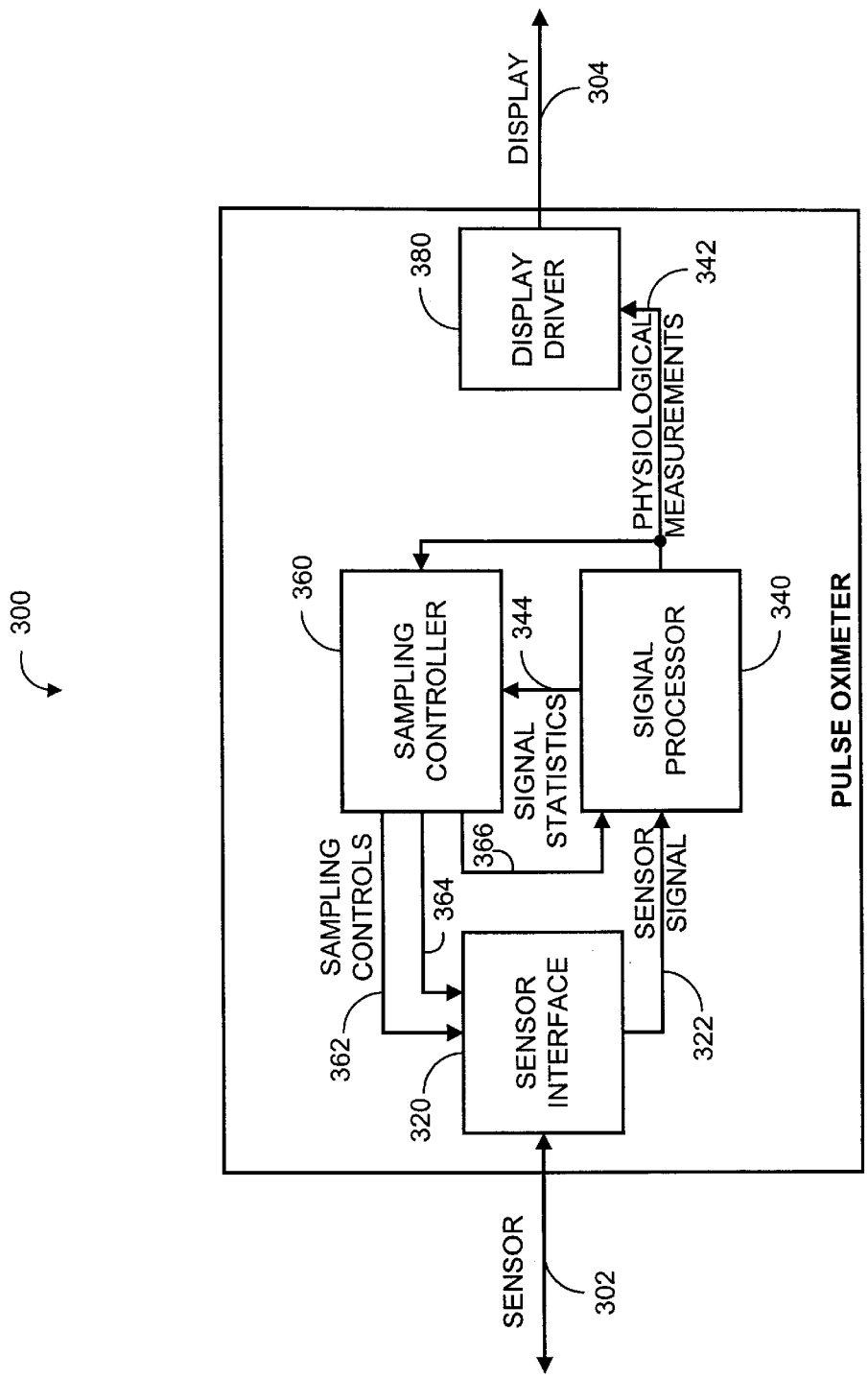
FIG. 3 is a top-level block diagram of a low power pulse oximeter.

FIG. 3 illustrates one embodiment of a low power pulse oximeter. The pulse oximeter 300 has a sensor interface 320, a signal processor 340, a sampling controller 360 and a display driver 380. The pulse oximeter 300 also has a sensor port 302 and a display port 304. The sensor port 302 connects to an external sensor, e.g. sensor 110 (FIG. 1). The sensor interface 320 drives the sensor port 302, receives a corresponding input signal from the sensor port 302, and provides a conditioned and digitized sensor signal 322 accordingly. Physiological measurements 342 are input to a display driver 380 that outputs to the display port 304. The display port 304 connects to a display device, such as a CRT or LCD, which a healthcare provider typically uses for monitoring a patient's oxygen saturation, pulse rate and plethysmograph.

As shown in FIG. 3, the signal processor 340 derives the physiological measurements 342, including oxygen saturation, pulse rate and plethysmograph, from the input signal 322. The signal processor 340 also derives signal statistics 344, such as signal strength, noise and motion artifact. The physiological measurements 342 and signal statistics 344 are input to the sampling controller 360, which outputs sampling controls 362, 364, 366 accordingly. The sampling controls 362, 364, 366 regulate pulse oximeter power dissipation by causing the sensor interface 320 to vary the sampling characteristics of the sensor port 302 and by causing the signal processor 340 to vary its sample processing characteristics, as described in further detail with respect to FIG. 4, below. Advantageously, power dissipation is responsive not only to output parameters, such as the physiological measurements 342, but also to internal parameters, such as the signal statistics 344.

Figure 4:
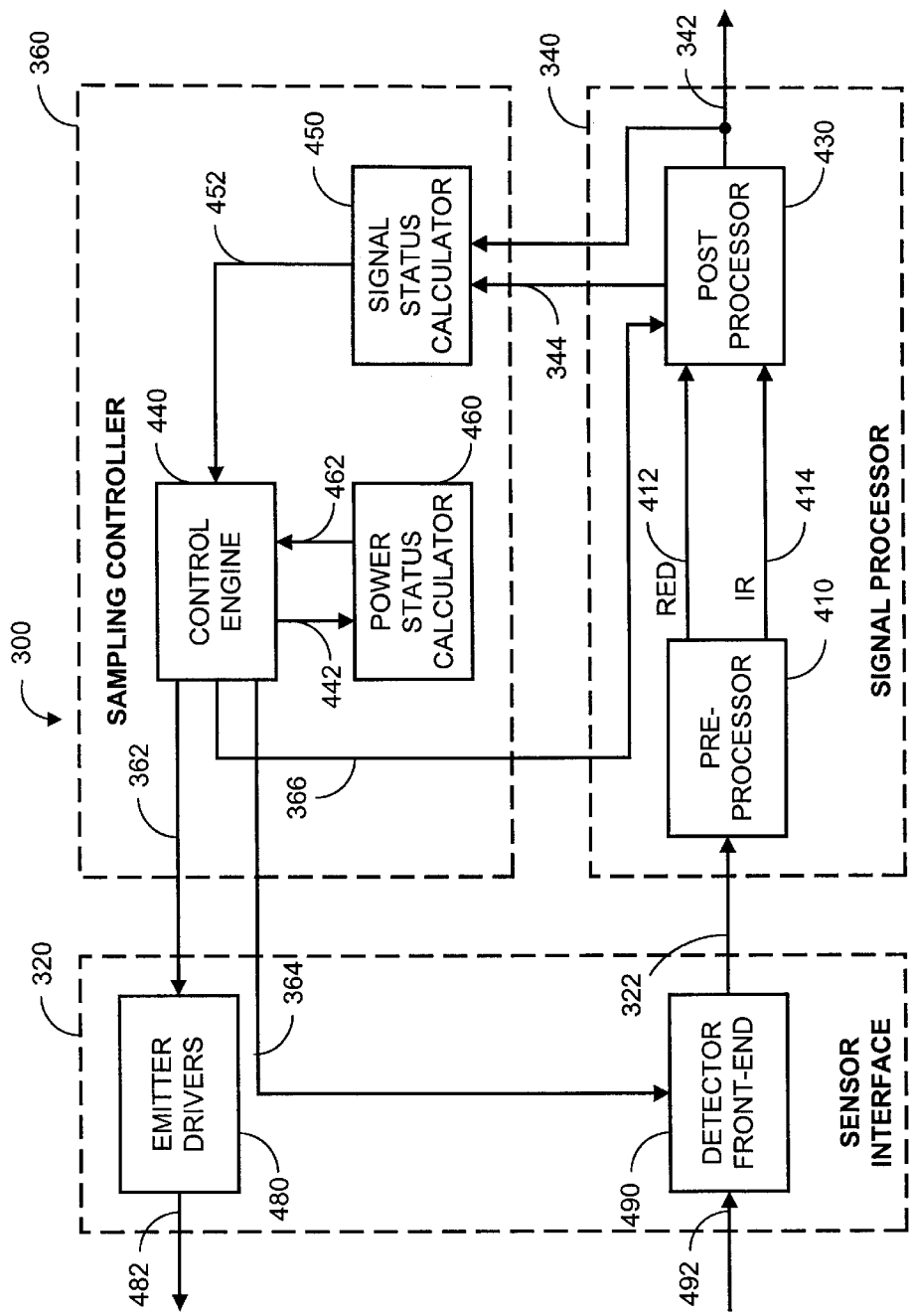
FIG. 4 is a detailed block diagram of a low power pulse oximeter illustrating a sensor interface, a signal processor and a sampling controller.

FIG. 4 illustrates further detail regarding the sensor interface 320, the signal processor 340 and the sampling controller 360. The sensor interface 320 has emitter drivers 480 and a detector front-end 490. The emitter drivers 480 are responsive to a sampling control 362, described below, and provide emitter drive outputs 482. The emitter drive outputs 482 activate the LEDs of a sensor attached to the sensor port 302 (FIG. 3). The detector front-end 490 receives an input signal 492 from a sensor attached to the sensor port 302 (FIG. 3) and provides a corresponding conditioned and digitized input signal 322 to the signal processor 340. A sampling control 364 controls power to the detector front-end 490, as described below.

As shown in FIG. 4, the signal processor 340 has a pre-processor 410 and a post processor 430. The pre-processor 410 demodulates red and IR signals from the digitized signal 322, performs filtering, and reduces the sample rate. The pre-processor provides a demodulated output, having a red channel 412 and an IR channel 414, which is input into the post-processor 430. The post processor 430 calculates the physiological measurements 342 and the signal statistics 344, which are output to a signal status calculator 450. The physiological measurements 342 are also output to a display driver 380 (FIG. 3) as described above. A pulse oximetry signal processor is described in U.S. Pat. No. 6,081,735 entitled "Signal Processing Apparatus," which is assigned to the assignee of the present invention and incorporated by reference herein.

Also shown in FIG. 4, the sampling controller 360 has a control engine 440, a signal status calculator 450 and a power status calculator 460. The control engine 440 outputs sampling controls 362, 364, 366 to reduce the power consumption of the pulse oximeter 300. In one embodiment, the control engine 440 advantageously utilizes multiple sampling mechanisms to alter power consumption. One sampling mechanism is an emitter duty cycle control 362 that is an input to the emitter drivers 480. The emitter duty cycle control 362 determines the duty cycle of the current supplied by the emitter drive outputs 482 to both red and IR sensor emitters, as described with respect to FIG. 5, below. Another sampling mechanism is a front-end control 364 that intermittently removes power to the detector front-end 490, as described with respected to FIG. 6, below. Yet another sampling mechanism is a data block overlap control 366 that varies the number of data blocks processed by the post processor 430. These various sampling mechanisms provide the flexibility to reduce power without sacrificing performance during, for example, high noise conditions or oxygen desaturation events, as described below in further detail.

The sampling controls 362, 364, 366 modify power consumption by, in effect, increasing or decreasing the number of input samples received and processed. Sampling, including acquiring input signal samples and subsequent sample processing, can be reduced during high signal quality periods and increased during low signal quality periods or when critical measurements are necessary. In this manner, the control engine 440 regulates power consumption to satisfy a predetermined power target, to minimize power consumption, or to simply reduce power consumption, as described with respect to FIGS. 8 and 10, below. The current state of the control engine is provided as a control state output 442 to the power status calculator 460. The control engine 440 utilizes the power status output 462 and the signal status output 452 to determine its next control state, as described with respect to FIGS. 9 and 11, below.

Further shown in FIG. 4, the signal status calculator 450 receives physiological measurements and signal statistics from the post processor 430 and determines the occurrence of an event or a low signal quality condition. An event determination is based upon the physiological measurements output 342 and may be any physiological-related indication that justifies the processing of more sensor samples and an associated higher power consumption level, such as an oxygen desaturation, a fast or irregular pulse rate or an unusual plethysmograph waveform to name a few. A low signal quality condition is based upon the signal statistics output 344 and may be any signal-related indication that justifies the processing of more sensor samples and an associated higher power consumption level, such as a low signal level, a high noise level or motion artifact to name a few. The signal status calculator 450 provides the signal status output 452 that is input to the control engine 440.

In addition, FIG. 4 shows that the power status calculator 460 has a control state input 442 and a power status output 462. The control state input 442 indicates the current state of the control engine 440. The power status calculator 460 utilizes an internal time base, such as a counter, timer or real-time clock, in conjunction with the control engine state to estimate the average power consumption of at least a portion of the pulse oximeter 300. The power status calculator 460 also stores a predetermined power target and compares its power consumption estimate to this target. The power status calculator 460 generates the power status output 462 as an indication that the current average power estimate is above or below the power target and provides this output 462 to the control engine 440.

Figure 5:
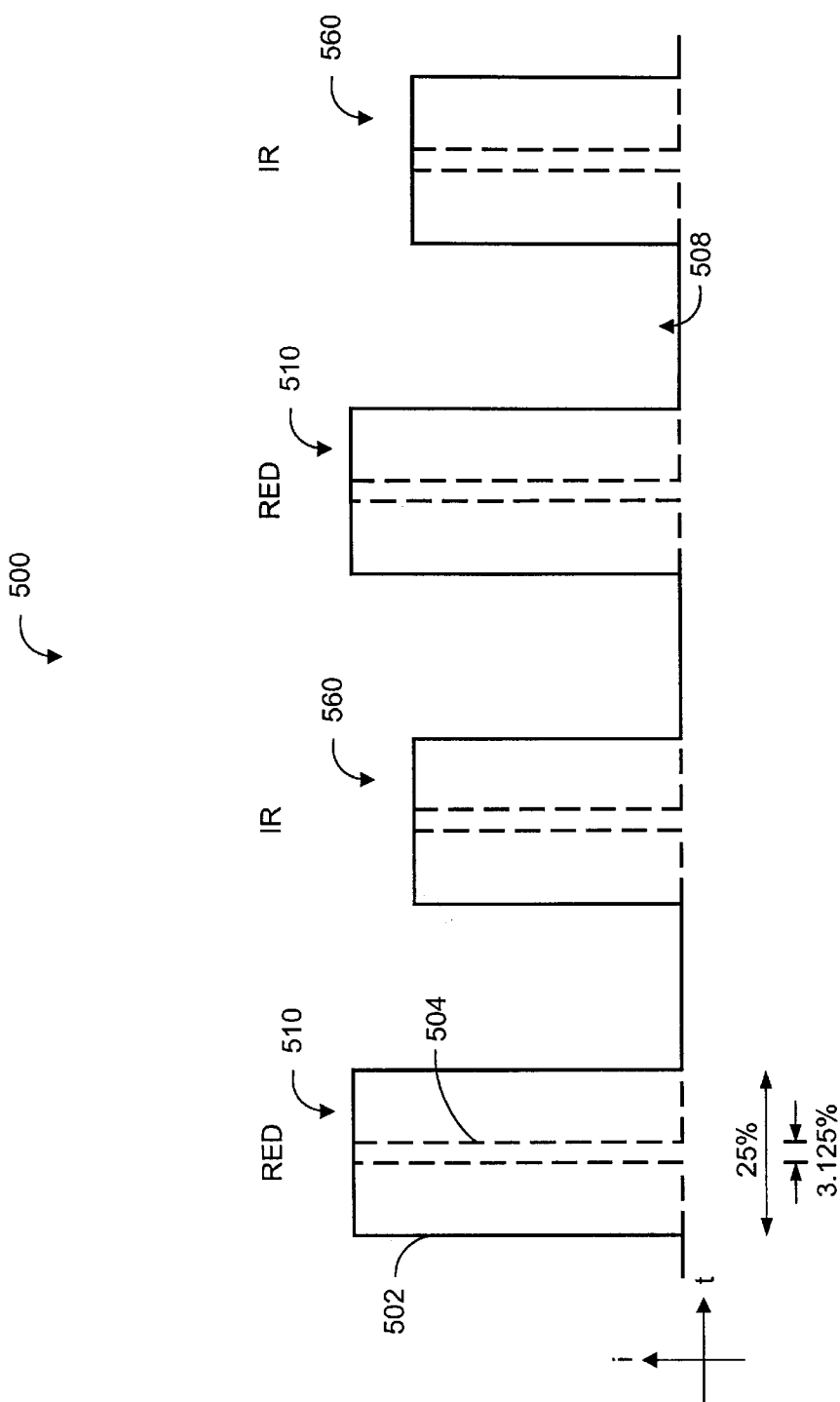
FIG. 5 is a graph of emitter drive current versus time illustrating variable duty cycle processing.

FIG. 5 illustrates emitter driver output current versus time. The graph 500 depicts the combination of a red LED drive current 510 and an IR drive current 560. The solid line graph 502 illustrates drive currents having a high duty cycle. The dashed line graph 504 illustrates drive currents having a low duty cycle. In a typical pulse oximeter, the duty cycle of the drive signals is constant and provides sufficient dark bands 508 to demodulate the detector response into red and IR channels. The emitter drivers 480 (FIG. 4), however, require a significant portion of the overall pulse oximeter power budget. Intermittently reducing the drive current duty cycle can advantageously reduce power dissipation without compromising signal integrity. As an example, a low power pulse oximeter implementation nominally consuming 500 mw may be able to reduce power consumption on the order of 70 mw by such drive current duty cycle reductions. In a preferred embodiment, the drive current duty cycle is varied within a range from about 25% to about 3.125%. In a more preferred embodiment, the drive current duty cycle is intermittently reduced from about 25% to about 3.125%. In conjunction with an intermittently reduced duty cycle or as an independent sampling mechanism, there may be a "data off" time period longer than one drive current cycle where the emitter drivers 480 (FIG. 4) are turned off. The detector front-end 490 (FIG. 4) may also be powered down during such a data off period, as described with respect to FIGS. 8 and 9, below.

Figure 6:
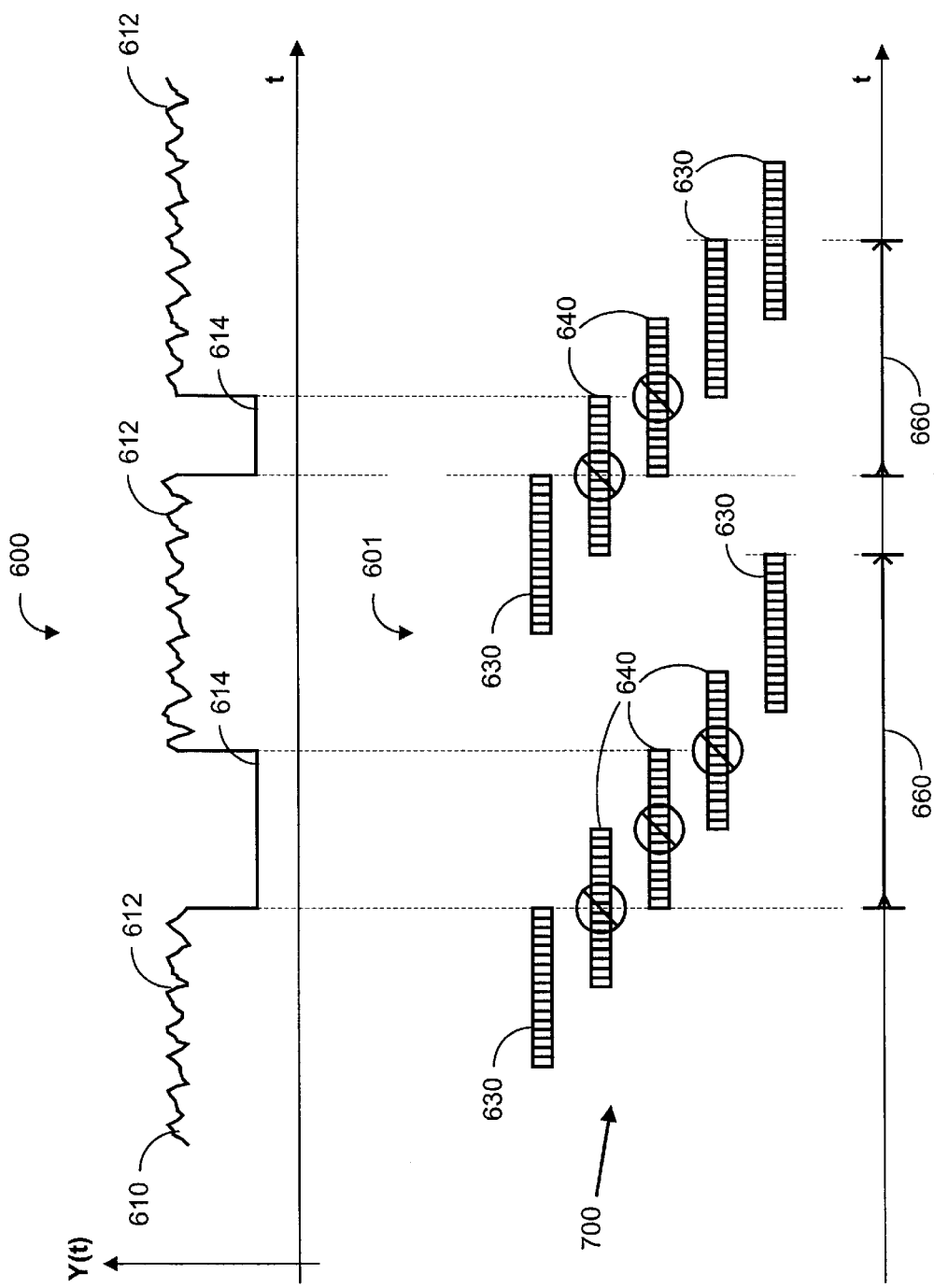
FIG. 6 is a graph of oxygen saturation versus time illustrating intermittent sample processing.

FIG. 6 is a graph 600 of a pre-processor output signal 610 over time depicting the result of intermittent sampling at the detector front-end 490 (FIG. 4). The output signal 610 is a red channel 412 (FIG. 4) or an IR channel 414 (FIG. 4) output from the pre-processor 410 (FIG. 4), which is input to the post processor 430 (FIG. 4), as described above. The output signal 610 has "on" periods 612, during which time the detector front-end 490 (FIG. 4) is powered-up and "off" periods 614, during which time the detector front-end 490 (FIG. 4) is powered-down. The location and duration of the on periods 612 and off periods 614 are determined by the front-end control 364 (FIG. 4).

Also shown in FIG. 6 is a corresponding timeline 601 of overlapping data blocks 700, which are "snap-shots" of the pre-processor output signal 610 over specific time intervals. Specifically, the post processor 430 (FIG. 4) processes a sliding window of samples of the pre-processor output signal 610, as described with respect to FIGS. 7A–B, below. Advantageously, the post processor 430 (FIG. 4) continues to function during off portions 614, marking as invalid those data blocks 640 that incorporate off portions 614. A freshness counter can be used to measure the time period 660 between valid data blocks 630, which can be displayed on a pulse oximeter monitor as an indication of confidence in the current measurements.

Figure 7A:
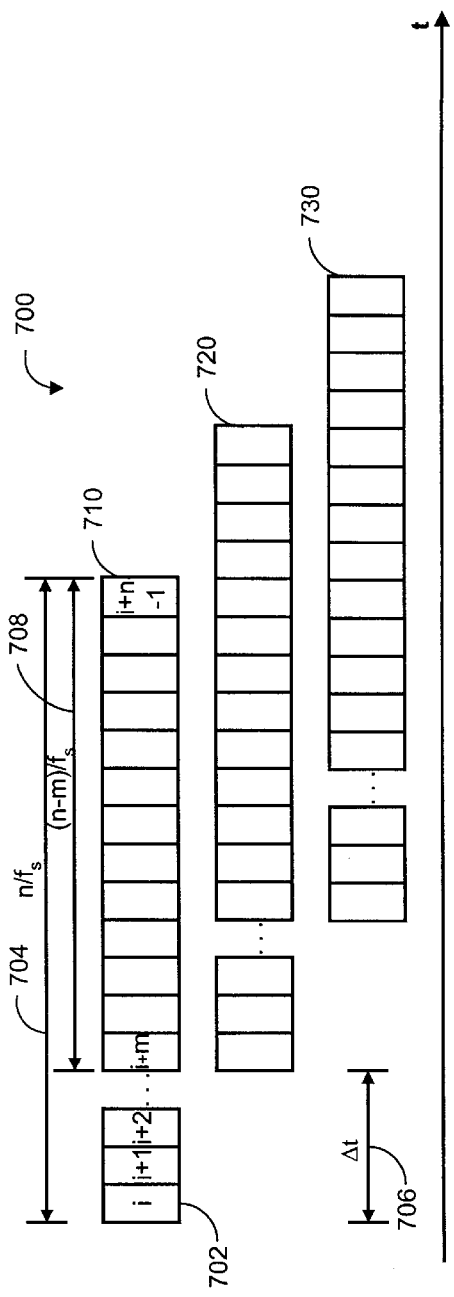
FIGS. 7A–B are graphs of data buffer content versus time illustrating variable data block overlap processing.
Figure 7B:
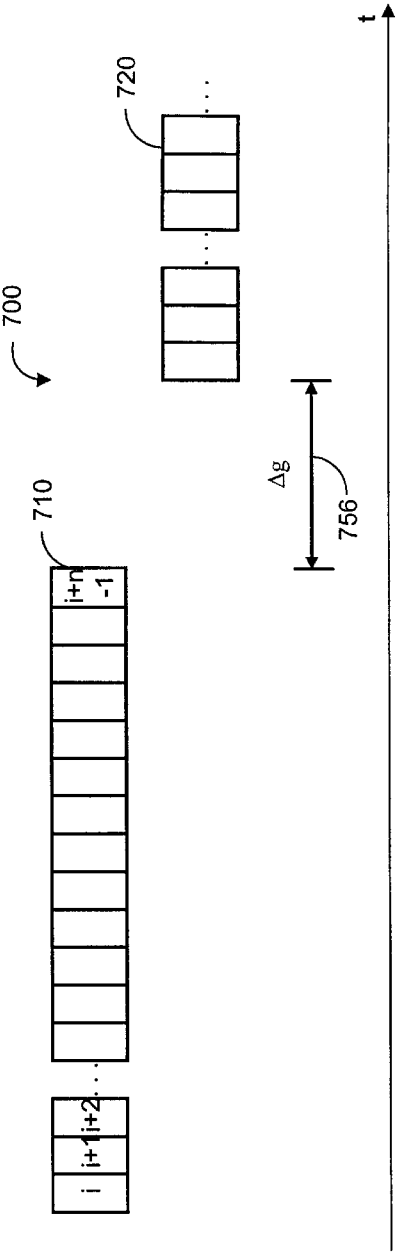

FIGS. 7A–B illustrate data blocks 700, which are processed by the post processor 430 (FIG. 4). Each data block 700 has n samples 702 of the pre-processor output and corresponds to a time interval 704 of $n/f_s$, where $f_s$ is the sample frequency. For example, in one embodiment n=600 and $f_s$=62.5 Hz. Hence, each data block time interval 704 is nominally 9.6 sec.

As shown in FIG. 7A, each data block 700 also has a relative time shift 706 from the preceding data block, where is an integral number of sample periods. That is, $=m/f_s$, where m is an integer representing the number of samples dropped from the preceding data block and added to the succeeding data block. In the embodiment described above, m=75 and =1.2 sec, nominally. The corresponding overlap 708 of two adjacent data blocks 710, 720 is $(n-m)/f_s$. In the embodiment described above, the overlap 708 is nominally 9.6 sec −1.2 sec=8.4 sec. The greater the overlap 708, i.e. the smaller the time shift 706, the more data blocks there are to process in the post-processor 430 (FIG. 4), with a corresponding greater power consumption. The overlap 708 between successive data blocks 710, 720 may vary from n−1 samples to no samples, i.e. no overlap. Also, as shown in FIG. 7B, there may be a sample gap 756 or negative overlap, i.e. samples between data blocks that are not processed by the post-processor, allowing further post-processor power savings. Sample gaps 756 may correspond to detector front-end off periods 614 (FIG. 6).

Figure 8:
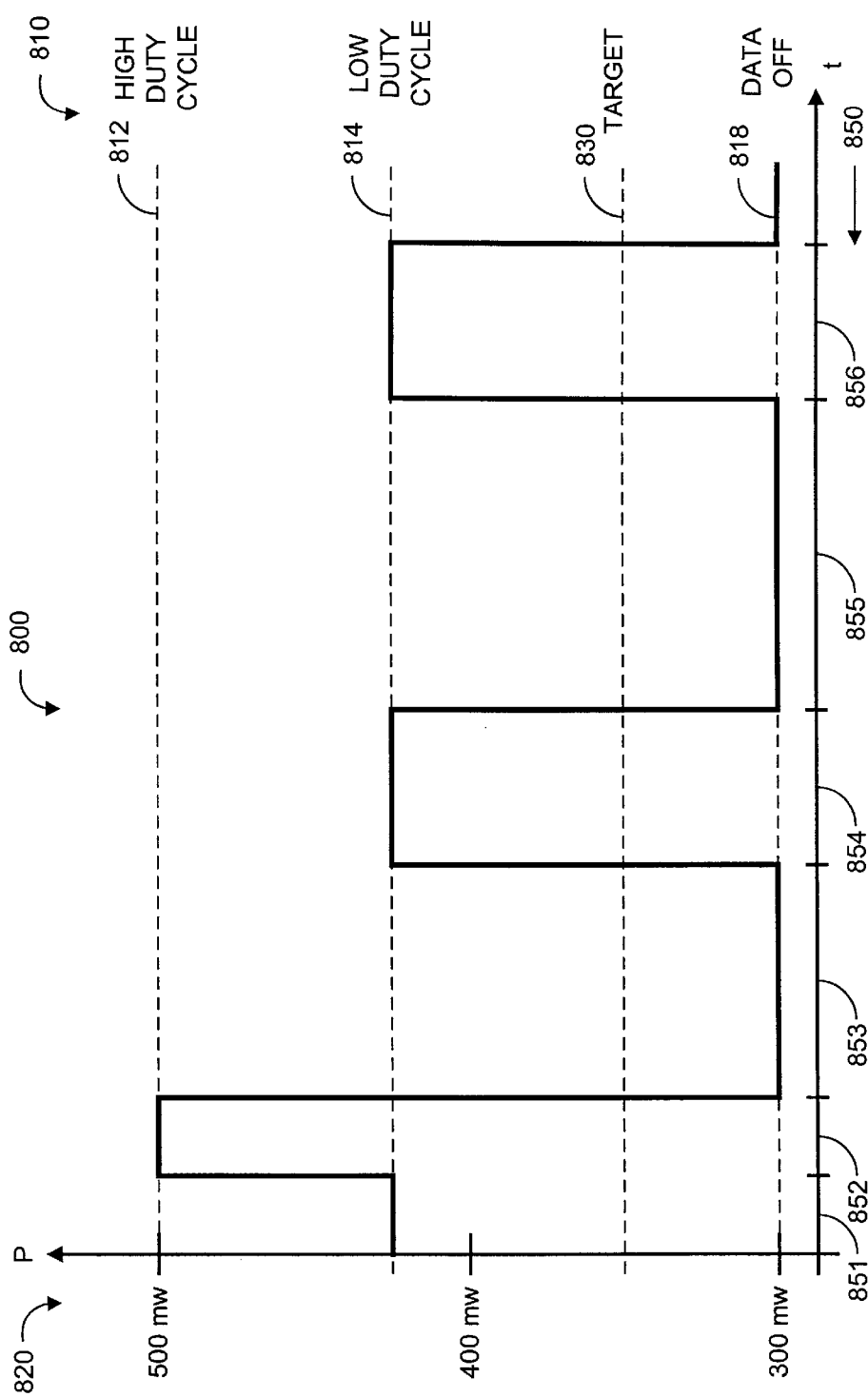
FIG. 8 is a graph of power versus time illustrating power dissipation conformance to an average power target using variable duty cycle and intermittent sample processing.

FIG. 8 illustrates an exemplar power consumption versus time profile 800 for the pulse oximeter 300 (FIG. 3) during various control engine states. In one embodiment, the control engine 440 (FIG. 4) has three states related to the sampling control outputs 362, 364 that affect pulse oximeter power consumption accordingly. One of ordinary skill in the art will recognize that the control engine 440 (FIG. 4) may have greater or fewer states and associated power consumption levels. The profile 800 shows the three control engine states 810 and the associated power consumption levels 820. These three states are high duty cycle 812, low duty cycle 814 and data off 818.

In the high duty cycle state 812, the control engine 440 (FIG. 4) causes the emitter drivers 480 (FIG. 4) to turn on sensor emitters for a relatively long time period, such as 25% on time for each of the red 510 and IR 560 drive currents. In the low duty cycle state 814, the control engine 440 (FIG. 4) causes the emitter drivers 480 (FIG. 4) to turn on sensor emitters for a relatively short time period, such as 3.125% of the time for each of the red 510 and IR 560 drive currents. In the data off state 818, the control engine 440 (FIG. 4) turns off the emitter drivers 480 (FIG. 4) and powers down the detector front-end 490 (FIG. 4). Also shown is a predetermined target power consumption level 830. The control engine 440 (FIG. 4) alters the sensor sampling of the pulse oximeter 300 (FIG. 3) so that the average power consumption matches the target level 830, as indicated by the power status output 462 (FIG. 4), except when overridden by the signal status output 452 (FIG. 4).

As shown in FIG. 8, power consumption changes according to the control states 810 during each of the time intervals 850. In a first time interval 851, the pulse oximeter is in a low duty cycle state 814 and transitions to a high duty cycle state 812 during a second time interval 852 due to an event or low quality signal. During a third time interval 853, the pulse oximeter is able to enter the data off state 818, during which time no sensor samples are processed. In a forth time interval 854, sensor samples are again taken, but at a low duty cycle 814. During the fifth and sixth time intervals 855, 856, sensor samples are shut off and turned on again as the pulse oximeter 300 (FIG. 3) alternates between the data off state 818 and the low duty cycle state 814 so as to maintain an average power consumption at the target level 830.

Figure 9:
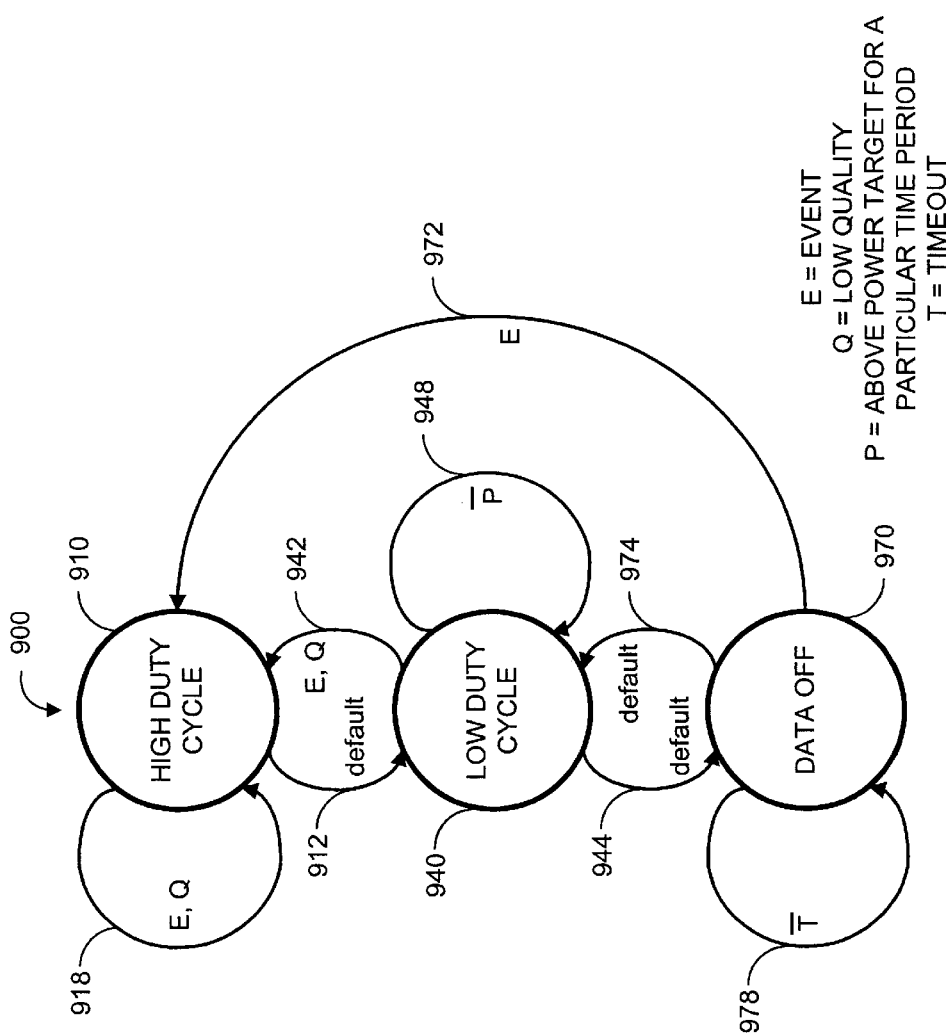
FIG. 9 is a state diagram of the sampling controller for variable duty cycle and intermittent sample processing.

FIG. 9 illustrates a state diagram 900 for one embodiment of the control engine 440 (FIG. 4). In this embodiment, there are three control states, high duty cycle 910, low duty cycle 940 and data off 970, as described with respect to FIG. 8, above. If the control state is data off 970, an event triggers a data-off to high-duty-cycle transition 972. If the control state is low duty cycle 940, an event similarly triggers a low-duty cycle to high-duty-cycle transition 942. In this manner, the occurrence of an event initiates high duty sensor sampling, allowing high fidelity monitoring of the event. Similarly, if the control state is low duty cycle 940, low signal quality triggers a low-duty cycle to high-duty-cycle transition 942. In this manner, low signal quality initiates higher duty sensor sampling, providing, for example, a larger signal-to-noise ratio.

Also shown in FIG. 9, if the control state is high duty cycle 910 and either an event is occurring or signal quality is low, then a null transition 918 maintains the high duty cycle state 910. If the pulse oximeter is not above the power target for more than a particular time interval, a null transition 948 maintains the low duty cycle state 940, so that sampling is turned-off only when necessary to track the power target. Further, if the control state is data off 970 and no time-out has occurred, a null transition 978 maintains the data off state 970, providing a minimum power consumption.

In addition, FIG. 9 shows that when the control state is in a high duty cycle state 910, if neither an event nor low signal quality are occurring, then a high-duty-cycle to low-duty-cycle transition 912 occurs by default. Also, if the control state is low duty cycle 940, if neither an event nor low signal quality are occurring and the power consumption is above the target level for longer than a particular time interval, a low-duty-cycle to data-off transition 944 occurs by default, allowing power consumption to come down to the target level. Further, if the control state is data off 970, if no event occurs and a timeout does occur, a data-off to low-duty-cycle transition 974 occurs by default, preventing excessively long periods of no sensor sampling.

Figure 10:
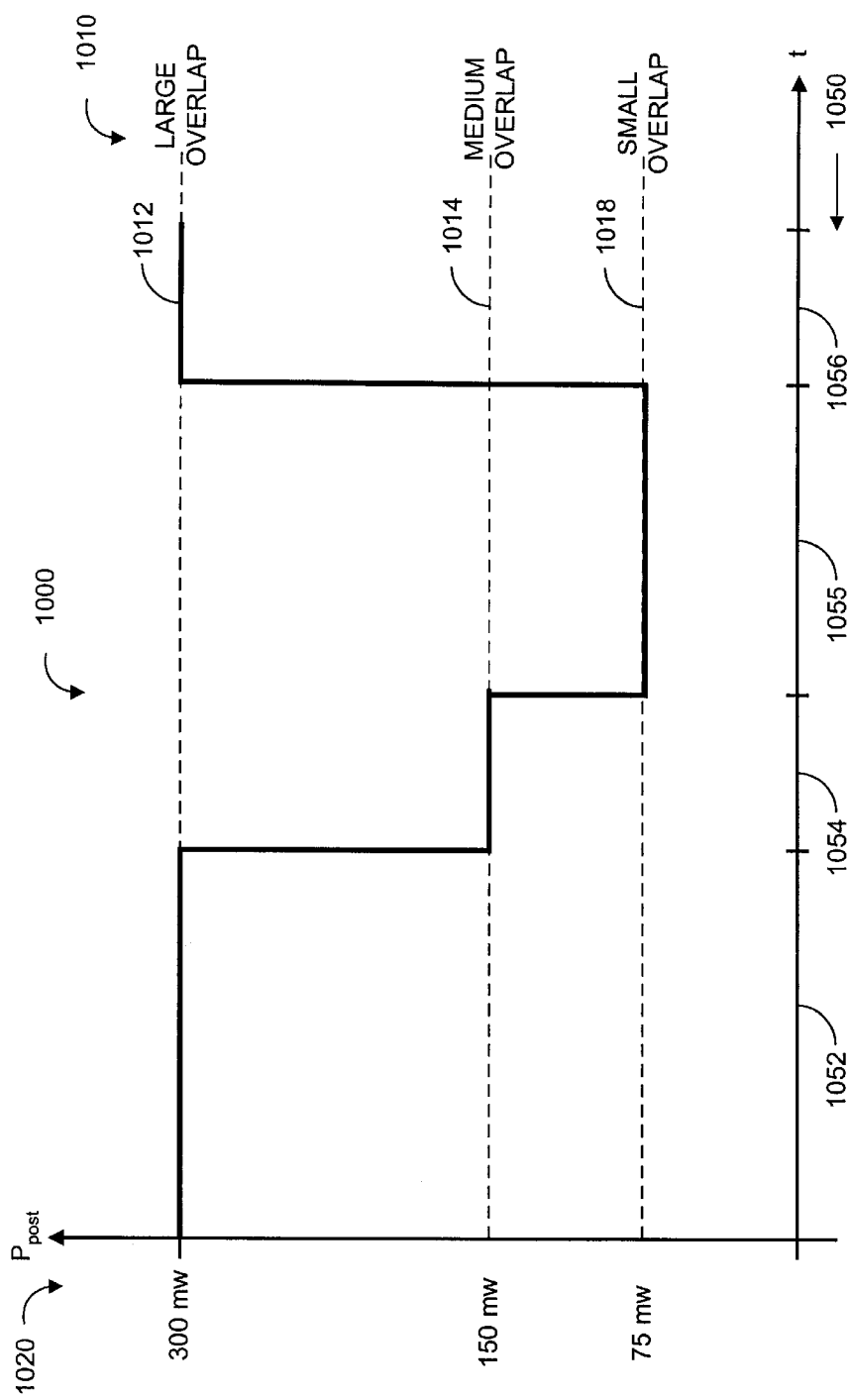
FIG. 10 is a graph of power versus time illustrating power dissipation using variable data block overlap processing.

FIG. 10 illustrates an exemplar power consumption versus time profile 1000 for the post processor 430 (FIG. 4) during various control engine states. In one embodiment, the control engine 440 (FIG. 4) has three states related to the sampling control output 366 (FIG. 4) that affect post processor power consumption accordingly. One of ordinary skill in the art will recognize that the control engine may have greater or fewer states and associated power consumption levels. The profile 1000 shows the three control engine states 1010 and the associated post processor power consumption levels 1020. These three states are large overlap 1012, medium overlap 1014 and small overlap 1018.

As shown in FIG. 10, in the large overlap state 1012, the control engine 440 (FIG. 4) causes the post processor to process data blocks that have a comparatively small time shift 706 (FIG. 7A), and the post processor exhibits relatively high power consumption under these conditions, say 300 mw. In the medium overlap state 1014, the control engine 440 (FIG. 4) causes the post processor to process data blocks that have a comparatively larger time shift 706 (FIG. 7A). For example, the data blocks may be time shifted twice as much as for the large overlap state 1012, and, as such, the post processor performs only half as many computations and consumes half the nominal power, say 150 mw. In the small overlap state 1018, the control engine 440 (FIG. 4) causes the post processor to process data blocks that have a comparatively large time shift. For example, the data blocks may be time shifted twice as much as for the medium overlap state 1014. As such, the post processor performs only a quarter as many computations and consumes a quarter of the nominal power, say 75 mw, as for the large overlap state 1012. In one embodiment, the control engine 440 (FIG. 4) alters the data block overlap of the post processor in conjunction with the duty cycle of the emitter drivers described with respect to FIG. 5, above, and the front-end sampling described with respect to FIG. 6, above, so that the average power consumption of the pulse oximeter matches a target level indicated by the power status output 462 (FIG. 4) or so that the power consumption is otherwise reduced or minimized.

In a preferred embodiment, data blocks are time shifted by either about 0.4 sec or about 1.2 sec, depending on the overlap state of the control engine 440 (FIG. 4). In a more preferred embodiment, the data blocks are varied between about 1.2 sec and about 4.8 sec. In a most preferred embodiment, the data blocks are time shifted by either about 1.2 sec, about 2.4 sec or about 4.8 sec, depending on the overlap state of the control engine 440 (FIG. 4). Although the post-processing of data blocks is described above with respect to only a few overlap states and a corresponding number of particular data block time shifts, there may be many overlap states and a corresponding range of data block time shifts.

Further shown in FIG. 10, power consumption 1020 changes according to the control states 1010 during each of the time intervals 1050. In a first time interval 1052, the post processor is in a large overlap state 1012 and transitions to a medium overlap state 1014 during a second time interval 1054, so as to meet a power target during a high signal quality period, for example. During a third time interval 1055, the post processor enters a small overlap state 1018, for example to meet a power target by further reducing power consumption. In a forth time interval 1056, the post processor transitions back to a large overlap state 1012, such as during an event or low signal quality conditions.

FIG. 11 illustrates a state diagram 1100 for one embodiment of the control engine 440 (FIG. 4). These states may function in parallel with, or in combination with, the sampling states described with respect to FIG. 9, above. In the illustrated embodiment, there are three control states, large overlap 1110, medium overlap 1140 and small overlap 1170, as described with respect to FIG. 10, above. If the control state is small overlap 1170, an event triggers a small overlap to large overlap transition 1172. If the control state is medium overlap 1140, an event similarly triggers a medium overlap to large-overlap transition 1142. In this manner, the occurrence of an event initiates the processing of more data blocks, allowing more robust signal statistics and higher fidelity monitoring of the event. Similarly, if the control state is medium overlap 1140, low signal quality triggers a medium overlap to large overlap transition 1142. In this manner, low signal quality initiates the processing of more data blocks, providing more robust signal statistics during lower signal-to-noise ratio periods.

Also shown in FIG. 11, if the control state is large overlap 1110 and either an event is occurring or signal quality is low, then a null transition 1118 maintains the large overlap state 1110. If the pulse oximeter is not above the power target for more than a particular time interval, a null transition 1148 maintains the medium overlap state 1140, so that reduced data processing occurs only when necessary to track the power target. Further, if the control state is small overlap 1170, a null transition 1178 maintains this power saving state until the power target is reached or an event or low signal quality condition occurs.

In addition, FIG. 11 shows that when the control state is in a large overlap state 1110, if neither an event nor low signal quality are occurring, then a large overlap to medium overlap transition 1112 occurs by default. Also, if the control state is medium overlap 1140, if the power consumption is above the target level for longer than a particular time interval and no low signal quality condition or event is occurring, a medium overlap to small overlap transition 1174 occurs, allowing power consumption to come down to the target level. Further, if the control state is small overlap 1170, if no event occurs but the power target has been met, a small overlap to medium overlap transition 1174 occurs.

A low power pulse oximeter embodiment is described above as having a power status calculator 460 (FIG. 4) and an associated power target. Another embodiment of a low power pulse oximeter, however, functions without either a power status calculator or a power target, utilizing the sampling controls 362, 364, 366 (FIG. 3) in response to internal parameters and/or output parameters, such as signal statistics 344 (FIG. 3) and/or physiological measurements 342 (FIG. 3) to reduce power consumption except during, say, periods of low signal quality and physiological events.

One of ordinary skill in the art will recognize that various state diagrams are possible representing control of the emitter drivers, the detector front-end and the post-processor. Such state diagrams may have fewer or greater states with differing transitional characteristics and with differing relationships between sampling mechanisms than the particular embodiments described above. In relatively simple embodiments of the control engine 440 (FIG. 4), only a single sampling mechanism is used, such as the sampling mechanism used to vary the duty cycle of the emitter drivers. The single sampling mechanism may be based only upon internal parameters, such as signal quality, only upon output parameters, such as those that indicate the occurrence of physiological events, or upon a combination of internal and output parameters, with or without a power target.

In relatively more complex embodiments of the control engine 440 (FIG. 4), sampling mechanisms are used in combination. These sampling mechanisms may be based only upon internal parameters, only upon output parameters, or upon a combination of internal and output parameters, with or without a power target. In a particular embodiment, the emitter duty-cycle, front-end duty-cycle and data block overlap sampling mechanisms described above are combined. A "reduced overlap" state relating to the post-processing of data blocks is added to the diagram of FIG. 9 between the "low duty cycle" state and the "data off" state. That is, sampling is varied between a high duty cycle state, a low duty cycle state, a reduced overlap state and a data off state in response to signal quality and physiological events, with or without a power target.

The low power pulse oximeter has been disclosed in detail in connection with various embodiments. These embodiments are disclosed by way of examples only and are not to limit the scope of the claims that follow. One of ordinary skill in the art will appreciate many variations and modifications.

What is claimed is:

1. A low power pulse oximeter comprising:

a sensor interface adapted to drive a pulse oximetry sensor and receive a corresponding input signal;

a processor that derives a physiological measurement corresponding to said input signal;

a display driver adapted to communicate said measurement to a display;

a controller gernerating a sampling control output to at least one of said sensor interface and said processor so as to reduce the average power consumption of said pulse oximeter consistent with a predetermined power target; and a calculator that derives a signal status output responsive to said input signal, said signal status output being communicated to said controller to override said sampling control output, wherein said signal status output indicates the occurence of a physiological event.

2. A low pulse oximeter comprising:

a sensor interface adapted to drive a pulse oximetry sensor and receive a corresponding input signal;

a processor that derives a physiological measurement corresponding to said input signal;

a display driver adapted to communicate said measurement to a display;

a controller generating a sampling control output to at least one of said sensor interface and said processor so as to reduce the average power consumption of said pulse oximeter consistent with a predetermined power target, wherein said sensor interface comprises a front-end adapted to receive said input signal from a detector portion of said sensor and to provide a corresponding digitized signal, and wherein said sampling control output determines a powered-down period of said front-end; and confidence indicator that is responsive to a duration of said powered-down period, said confidence indicator communicated to said display driver.

3. A low power pulse oximeter comprising:

a sensor interface adapted to drive a pulse oximetry sensor and receive a corresponding input signal;

a processor that derives a physiological measurement corresponding to said input signal;

a display driver adapted to communicate said measurement to a display;

a controller generating a sampling control output to at least one of said sensor interface and said processor so as to reduce the average power consumption of said pulse oximeter consistent with a predetermined power target;

plurality of data blocks responsive to said input signal, wherein said sampling control output determines a time shift of successive ones of said data blocks.

4. The low power pulse oximeter according to claim 3 wherein said time shift varies in the range of about 1.2 seconds to about 4.8 seconds.

5. A low power pulse oximetry method comprising the steps of:

storing a power target;

receiving an input signal from a pulse oximetry sensor;

calculating signal status related to said input signal;

calculating power status related to said power target; and sampling based upon the result of said calculating signal status and said calculating power status steps.

6. The low power pulse oximetry method according to claim 5 wherein said calculating signal status step comprises the substeps of:

receiving a signal statistic related to said input signal;

receiving a physiological measurement related to said input signal;

determining a low signal quality condition from said signal statistic;

determining an event occurrence from said physiological measurement; and indicating an override based upon said low signal quality condition or said event occurrence.

7. The low power pulse oximetry method according to claim 6 wherein said calculating power status step comprises the substeps of:

estimating an average power consumption for at least a portion of said pulse oximeter; and indicating an above power target condition when said average power consumption is above said power target.

8. The low power pulse oximetry method according to claim 7 wherein said sampling step comprises the substep of decreasing sampling as the result of said above power target condition, except during said override.

9. The low power pulse oximetry method according to claim 6 wherein said sampling step comprises the substep of increasing sampling as the result of said override.

10. A low power pulse oximetry method comprising the steps of:

detecting an override related to a measure of signal quality or a physiological measurement event;

increasing said pulse oximeter to a higher power level when said override exists;

reducing said pulse oximeter to a lower power level if said override does not exist;

predetermining a target power level for a pulse oximeter; and cycling between said lower power lever and said higher power level so that an average power consumption is consistent with said target power level.

11. A low power pulse oximetry method comprising the steps of:

detecting an override related to a measure of signal quality or a physiological measurement event;

increasing said pulse oximeter to a higher power level when said override exists; and reducing said pulse oximeter to a lower power level if said override does not exist, wherein said reducing step comprises the substep of decreasing the duty cycle of an emitter driver output.

12. A low power pulse oximetry method comprising the steps of:

detecting an override related to a measure of signal quality or a physiological measurement event;

increasing said pulse oximeter to a higher power level when said override exist;

reducing said pulse oximeter to a lower power level if said override does not exist, wherein said reducing step comprises the substep of powering-down a detector front-end; and displaying a confidence indication related to the duration of said powering-down substep.

13. A low power pulse oximetry method comprising the steps of:

detecting an override related to a measure of signal quality or a physiological measurement event;

increasing said pulse oximeter to a higher power level when said override exists;

reducing said pulse oximeter to a lower power level if said override does not exist, wherein said reducing step comprises the substep of increasing the time-shift of post-processor data blocks.

14. A low power pulse oximeter comprising:

a sensor interface adapted to receive an input signal from a sensor;

a signal processor configured to communicate with said sensor interface and to generate an internal parameter responsive to said input signal; and a sampling controller responsive to said internal parameter so as to generate a sampling control to alter the power consumption of at least one of said senor interface and said signal processor, wherein said sampling controller is responsive to a predetermined power target in combination with said internal parameter so as to generate a sampling control to alter the power consumption of at least one of said sensor interface and said signal processor.

15. The low power pulse oximeter according to claim 14 wherein said signal processor is configured to generate an output parameter and said sampling controller is responsive to a combination of said internal and output parameters and said power target so as to generate a sampling control to alter the power consumption of at least one of said sensor interface and said signal processor.

16. A low power pulse oximeter comprising:

a sensor interface adapted to receive an input signal from a sensor;

a signal processor configured to communicate with said sensor interface and to generate an internal parameter responsive to said input signal; and a sampling controller responsive to said internal parameter so as to generate a sampling control to alter the power consumption of at least one of said sensor interface and said signal processor, wherein said processor generates a plurality of data blocks corresponding to said input signal, each of said data blocks having a time shift from a preceding one of said data blocks, said sampling control determining the amount of said time shift.

17. A low power pulse oximeter comprising:

an interface means for communicating with a sensor;

a processor means for generating an internal parameter and an output parameter; and a controlller means for selectively reducing the power consumption of at least one of said interface means and said processor means based upon said parameters, wherein said interface means comprises a driver means for determining the duty cycle of emitter current to said sensor, and said driver means is responsive to said controller means.

18. A low power pulse oximeter comprising:

an interface means for communicating with a sensor;

a processor means for generating an internal parameter and an output parameter; and a controller means for selectively reducing the power consumption of at least one of said interface means said processor means based upon said parameters, wherein said processor means comprises a post-processor means for determining a time shift between data blocks, and wherein said post-processor means is responsive to said controller means.

19. a low power pulse oximeter comprising:

an interface means for communication with a sensor;

a processor means for generating an internal parameter and an output parameter; and a controller means for selectively reducing the power consumption of at least one of said interface means and said processor means based upon said parameters, wherein said controller means comprises:

a power status calculator means for generating a power indication of power consumption relative to a power target, and a control engine means in communications with said power status calculator means for generating a sampling control responsive to said power indication.

* * * * *

UNITED STATES PATENT AND TRADEMARK OFFICE
CERTIFICATE OF CORRECTION

PATENT NO.     : 6,697,658 B2
DATED          : February 24, 2004
INVENTOR(S)    : Al-Ali Ammar It is certified that error appears in the above-identified patent and that said Letters Patent is hereby corrected as shown below:

Title page,
Item [74], *Attorney, Agent, or Firm*, delete "Knobbe Martens Olson & Bear LLP" and insert -- Knobbe, Martens, Olson & Bear, LLP --.

Column 11,
Line 51, delete "occurence" and insert -- occurrence --.
Line 52, after "low" and insert -- power --.

Column 12,
Line 3, insert -- a -- before "confidence".
Line 19, insert -- a -- before "plurality".

Column 13,
Line 5, delete "lever" and insert -- level --.
Line 25, delete "exist" and insert -- exists --.
Line 37, after "exists;" insert -- and --.
Line 51, delete "senor" and insert -- sensor --.

Column 14,
Line 26, delete "controlller" and insert -- controller --.
Line 38, after "means" insert -- and --.
Line 45, delete "a" and insert -- A --.
Line 46, delete "communication" and insert -- communicating --.

Signed and Sealed this

Twenty-fifth Day of October, 2005

JON W. DUDAS
*Director of the United States Patent and Trademark Office*